United States Patent [19]
Reeves

[11] Patent Number: 4,644,394
[45] Date of Patent: Feb. 17, 1987

[54] APPARATUS FOR INSPECTING AN EXTERNALLY THREADED SURFACE OF AN OBJECT

[76] Inventor: Dale Reeves, 821 Pinegrove, Longview, Tex. 75604

[21] Appl. No.: 815,376

[22] Filed: Dec. 31, 1985

[51] Int. Cl.⁴ ............................................. H04N 7/18
[52] U.S. Cl. ............................. 358/101; 33/199 B; 356/398; 358/106; 358/210
[58] Field of Search ............... 358/101, 106, 107, 210, 358/903; 250/223 B; 356/237, 398; 33/199 R, 199 B

[56] References Cited

U.S. PATENT DOCUMENTS

| | | | |
|---|---|---|---|
| 3,667,846 | 6/1972 | Nater et al. | 250/572 |
| 3,832,724 | 8/1974 | Duval | 358/100 |
| 3,924,953 | 12/1975 | Allard | 356/398 |
| 3,930,141 | 12/1975 | Koyama | 382/8 |
| 4,025,201 | 5/1977 | Deane | 358/106 |
| 4,255,762 | 3/1981 | Takeyasu et al. | 358/210 |
| 4,315,688 | 2/1982 | Pryor | 356/398 |
| 4,324,049 | 4/1982 | Blose | 33/199 B |
| 4,364,088 | 12/1982 | Kubota | 358/106 |
| 4,393,401 | 7/1983 | Gorenflo et al. | 358/107 |
| 4,435,641 | 3/1984 | Hajime | 250/223 B |
| 4,486,776 | 12/1984 | Yoshida | 358/106 |
| 4,511,918 | 4/1985 | Lemelson | 358/101 |

*Primary Examiner*—Howard W. Britton
*Attorney, Agent, or Firm*—Charles D. Gunter, Jr.

[57] ABSTRACT

An apparatus and method are shown for inspecting the externally threaded surface of an object such as a pipe. A video camera is mounted in a translational frame for movement in x,y,z planes. The translational frame is mounted in a rotational assembly which rotates the frame about the circumference of the pipe threads to be inspected. The video signals from the camera are digitized and sent to a computer processor where the signals are interpreted to position the camera as it moves linearly along the axis of the pipe threads and to detect defects and discontinuities in the threaded surface of the pipe being inspected.

11 Claims, 11 Drawing Figures

APPARATUS FOR INSPECTING AN EXTERNALLY THREADED SURFACE OF AN OBJECT

BACKGROUND OF THE INVENTION

1. Field of the Invention

The present invention relates to an apparatus and method for inspecting threaded objects and, specifically, for inspecting the externally threaded surface of an object such as a pipe.

2. Decription of the Prior Art

There is a need in many industries for an apparatus and method for measuring the thread dimensions of several different elements of a threaded surface, such as thread height, thread lead, thread taper, pitch diameter, chamfer dimensions, as well as discontinuities and defects in the thread surface to a high degree of accuracy.

The critical gaging of these thread elements is necessary due to the critical nature of many applications in which the threaded object is used. For instance, in oil and gas wells, the weight of a string of well pipe may exceed 500,000 pounds. The threaded pipe couplings must support this load and a thread failure can be extremely costly in money, as well as many times in the loss of human life. As a result, the American Petroleum Institute has published specifications which oil and gas well casing and tubing must meet. Other critical applications for thread inspection include the nuclear industry where threaded surfaces on nuclear rods must be inspected with a high degree of accuracy.

Electronic gages have been developed in recent years for use in inspecting the threaded surfaces of pipe. An example of such a gage can be found in U.S. Pat. No. 4,324,049 to Blose, issued Apr. 13, 1982, entitled "Gaging System and Method". Such gages typically employ contact feelers which contact the threaded surface to be measured at set points and mechanically measure the tolerances. One disadvantage of such devices is that the contact feelers can become worn with usage or become out of adjustment. Also, because the gage only takes a reading when the feeler is contacting the pipe, 100% coverage of the threaded surface during the inspection is not possible.

U.S. Pat. No. 4,315,688, to Pryor, issued Feb. 16, 1982, entitld "Electro-optical Sensor Systems For Thread and Hole Inspection", shows an apparatus for inspecting threaded objects, such as bolts, moving on a conveyor line past the inspection station. A detector having a light sensitive member picks up reflected light and produces analog output which is used to determine the quality of the threads. The light sensitive member has a light sensitive area sufficiently small to resolve the individual threads of the threaded object, to check to see that the correct number of threads are present.

It is also known to use video technology in the packaging and container industries. For instance, U.S. Pat. No. 4,435,641, issued Mar. 6, 1984, to Hajime, shows an inspection apparatus used to examine a bottle mouth as well as the bottle bottom simultaneously. The apparatus is not used to inspect externally threaded surfaces.

Inspection devices which use video cameras to inspect the interior of pipe by remotely reproducing a video image of the pipe interior are also known. U.S. Pat. No. 4,255,762, issued Mar. 10, 1981, to Takeyasu, et. al., shows such a device which is inserted into the interior of the pipe being inspected. The device is not revolved about the pipe exterior to inspect externally threaded surfaces.

Applicant is not aware of any prior art devices used to inspect externally threaded surfaces, such as pipe threads, in which a video camera is rotated about the stationary pipe to produce video signals, and in which the video signals are digitized and analyzed to determine the thread characteristics and to locate defects and abnormalities in the threaded surfaces.

SUMMARY OF THE INVENTION

The apparatus of the invention is used to inspect the externally threaded surface of an object, such as a pipe. The apparatus has a studio section including a light source for illuminating the threaded surface to be inspected, a mirror system for directing the light from the light source, and a video camera for receiving the directed light, for forming an optical image of the illuminated threaded surface, and for converting the optical image into electrical video signals.

Positioning means are provided as a part of the apparatus including a translational frame on which the studio section is mounted for moving the studio section in x,y,z planes in order to position the studio section about the object to be inspected at a starting point and for moving the studio section linearly along the longitudinal axis of the pipe.

A rotational assembly is provided for spinning the translational frame and studio section cricumferentially about the pipe exterior as the translational frame moves the studo section linearly along the longitudinal axis of the pipe.

An encoding means converts the video signals from the studio camera into digital information representative of special information in the optical images viewed by the video camera.

Processing means receive and interpret the digitized information provided by the encoding means, the processing means including a position controller for controlling the movement of the translational frame in responce to the digitized information, and an image processor for comparing the digitized information to a programmed standard for analyzing the thread characteristics and for detecting defects in the threaded surface being inspected.

The above as well as additional objects, features, and advantages of the invention will become apparent in the following detailed description.

DESCRIPTION OF THE PREFERRED EMBODIMENT

The inspection apparatus of the invention includes a studio section, a positioning section, a rotational assembly, an encoding section, and a computer processing section. Each of these sections will be discussed in turn with reference to FIGS. 1, 2, 3 and 4. A pipe conveyor and pipe clamp are used to provide pipe to the device and hold the pipe stationary during the inspection process, and these features of the invention will be discussed with reference to FIGS. 5 and 7-10.

Figure 1:
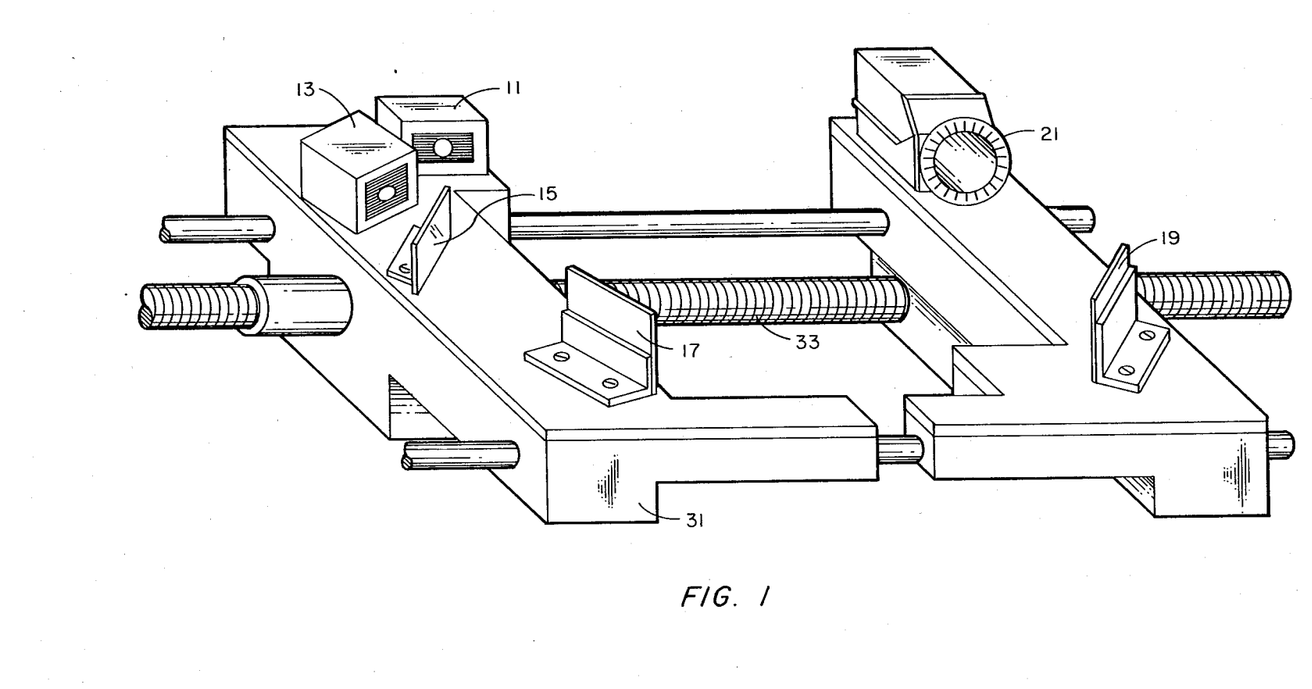
FIG. 1 is a perspective view of the translational frame of the apparatus of the invention showing the light source, mirrors and video camera mounted thereon.

As shown in FIG. 1, the studio section of the apparatus preferably includes two light sources 11,13 for illuminating the threaded surface to be inspected, a mirror system 15,17,19 for directing the light from the light sources, and a video camera 21 for receiving the directed light, for forming an optical image of the illuminated threaded surface, and for converting the optical image into electrical video signals. The studio components are all commercially available and can be purchased from Prothon Division of Video Tek, Inc., of Parsippany, New Jersey.

Figure 6:
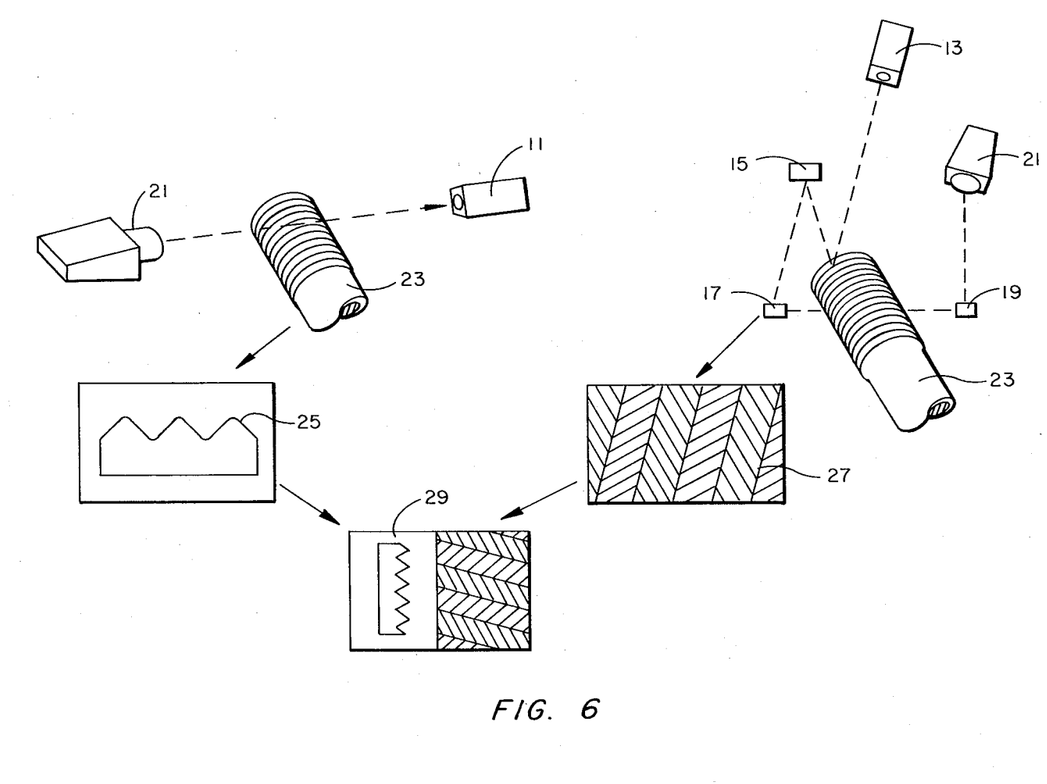
FIG. 6 is a simplified schematic view of the operation of the studio section of the apparatus showing the profile and thread surface optical images used in the inspection process.
Figure 7:
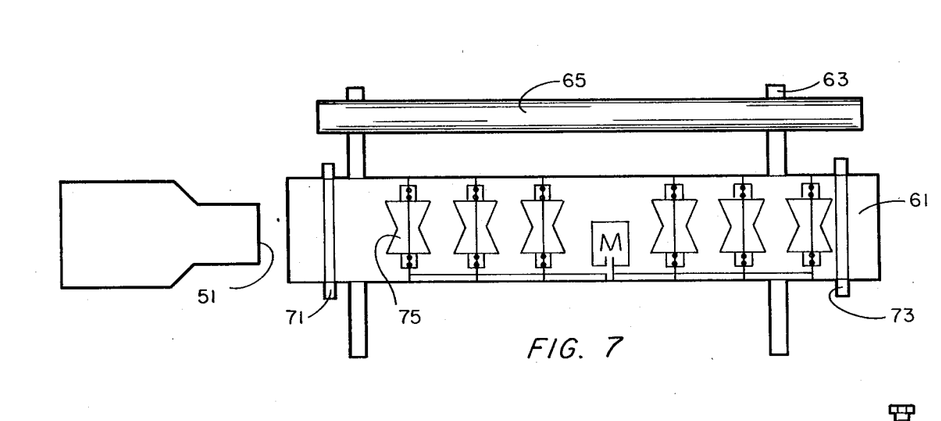
FIG. 7 is simplified schematic view of a pipe conveyor used to provide a pipe to the pipe clamp of the apparatus.

As shown schematically in FIG. 6, the studio section preferably includes one light source 11 arranged tangent to the object to be inspected, in this case pipe 23. That is, the light source 11 provides light tangent to the circle defined by the circumference of the threaded surface to be inspected. Light source 11 provides an illuminated profile of the threaded surface 25 which can be displayed on a video monitor. The second light source 13 is arranged perpendicular to the externally threaded surface to be inspected and normal to the central, longitudinal axis of the pipe to directly illuminate the threaded surface to form a surface optical image 27 in the video camera, the output of which can be displayed in composite form on a video monitor 29.

The light source or sources 11,13 are preferably pulsed collimated light sources such as a collimated laser. The video camera 21 can be obtained commercially having 370 active pixels per scan, 240 scans per field and 2 fields per frame. This provides a 2 mil convergence per pixel. The camera can operate at approximately 18 frames per second without image retention problems.

The apparatus of the invention also includes a positioning means including a translational frame 31 on which the studio section is mounted for moving the studio section in x,y,z planes in order to position the studio section about the pipe to be inspected at a starting point and for moving the studio section linearly along the longitudinal axis of the pipe during the inspection process. The translational frame includes one or more drive screws 33 (FIG. 1) which are operated by computer controlled drive motor/encoders, 35 (see FIGS. 2 and 3), through drive gears (such as gears 37) for rapidly adjusting the position of the studio components in x, y directions during the inspection process. This is accomplished by actuating the drive motor/encoder 35 (FIG. 2) which causes drive screw 33 (FIG. 1) to move the two halves 30, 32 of the x, y, z plane along the slide bars 34, 36. The position of the studio components can also be varied in a Z direction, or plane, as will be explained. The X, Y and Z planes or directions of movement are illustrated schematically in FIG. 4. Translational frames of the type under consideration are known to those skilled in the art and are commercially available from Klinger Scientific Corporation of Richmond Hill, New York.

A rotational assembly is provided for spinning the translational frame and studio section circumferentially about the pipe exterior as the translational frame moves the studio section linearly along the longitudinal axis of the pipe. The rotational assembly includes a rotatable shaft 39 having a yoke 41 at one end for mounting the translational frame 31. The shaft 39 is mounted generally horizontally to the plane of the ground on a base 43 which is provided with an electric drive motor 45 for rotating the shaft 39 and, in turn, the translational frame 31 and studio section. A pair of rollers 47,49 can be provided on the base 43 in contact with the yoke 41 to maintain the rotational stability of the assembly. A counterweight 101 can also be provided to balance the yoke 41. Once the translational frame 31 is assembled on the yoke 41, a pipe receiving opening 51 is formed (see FIG. 5) which is axially alignable with a pipe to be inspected.

Figure 2:
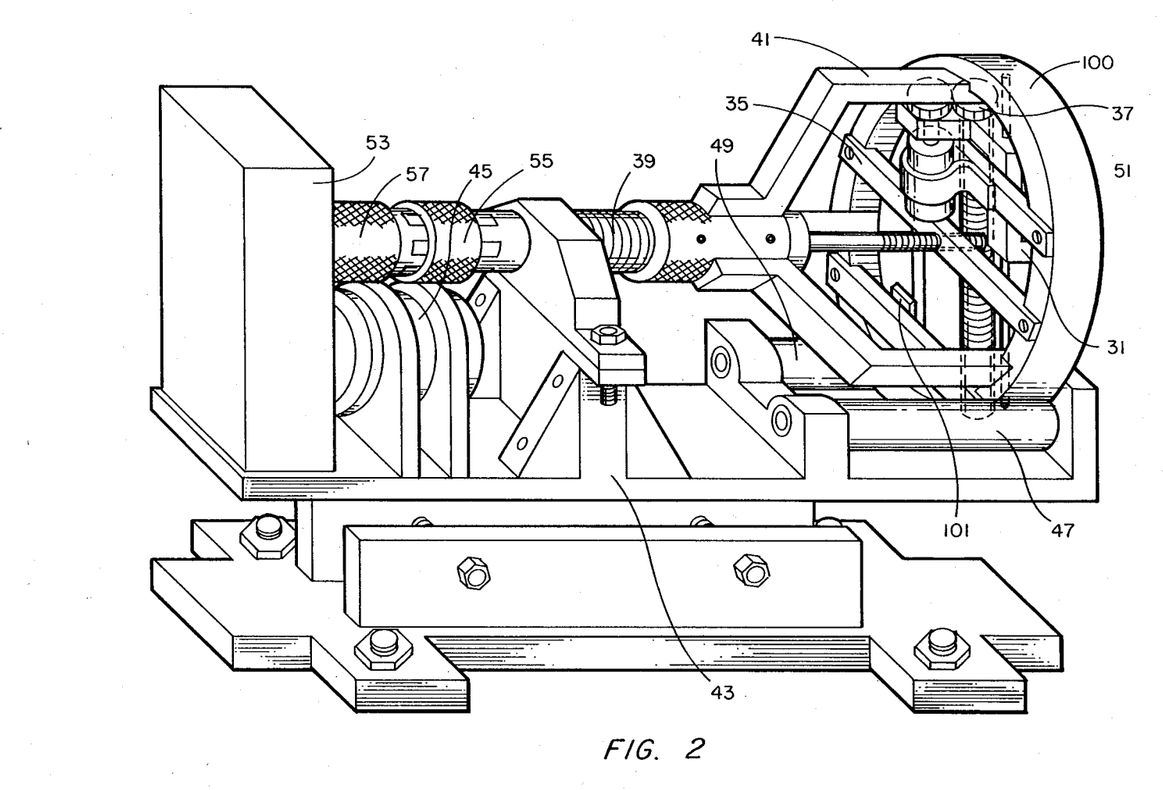
FIG. 2 is a side perspective view of the rotational assembly used to spin the translational frame about the pipe to be inspected.
Figure 3:
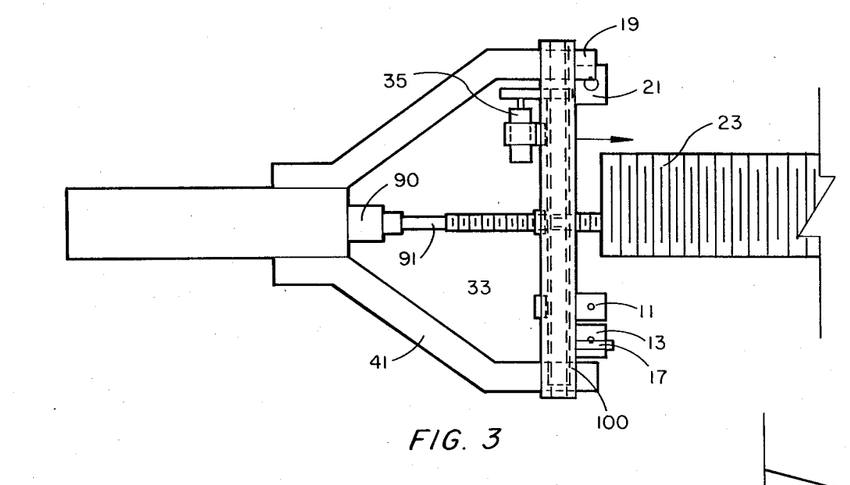
FIG. 3 is a top perspective view of the yoke of the rotational assembly and showing further details of the translational frame.
Figure 4:
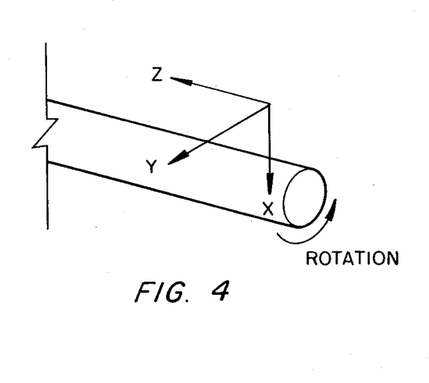
FIG. 4 is a schematic diagram illustrating the X, Y, Z movement of the translational frame.
Figure 5:
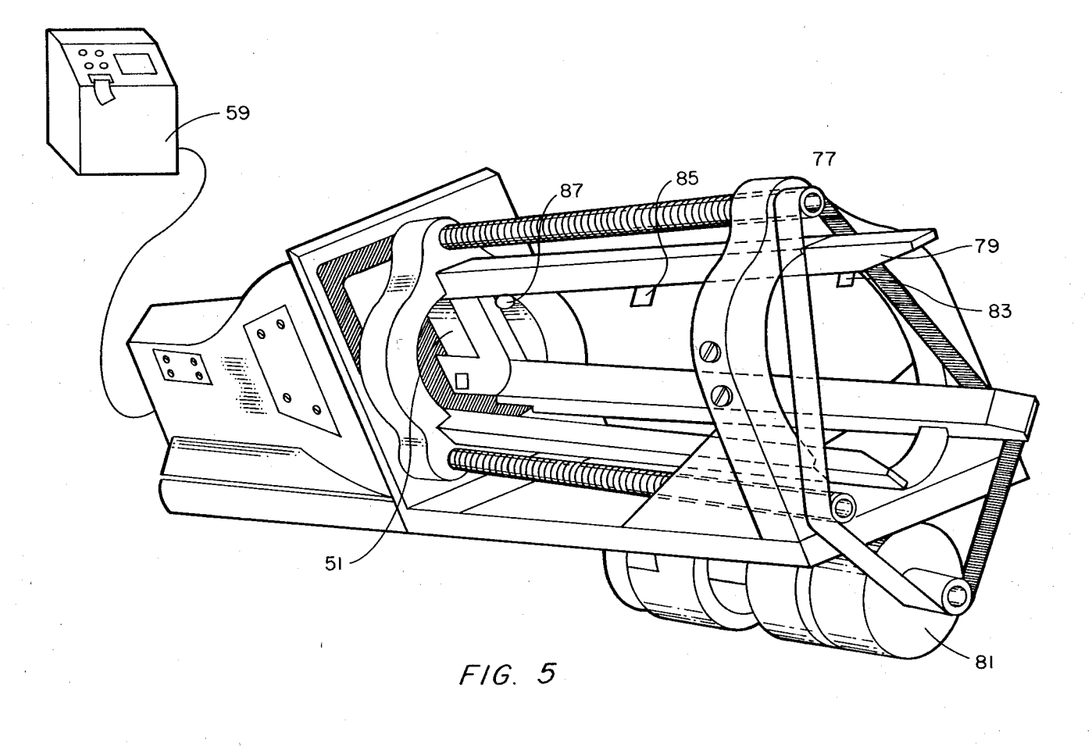
FIG. 5 is a perspective view of the exterior of the apparatus of the invention, showing a pipe clamp used to position a pipe within the apparatus.

As best seen in FIGS. 2 and 3 a computer controlled drive motor/encoder 90 and screw 91 are used to move the translational frame 31 linearly along the exterior of the pipe in a Z direction (FIG. 4). Actuation of the drive motor/encoder 90 causes screw 91 to move the cross bar 94. This, in turn, moves the mounting ring 100 and the translational frame along the yoke arms 41 in the Z direction. The translational frame is set back within the yoke so that the distance "d" in FIG. 3 is at least 12 inches. Since the threads to be inspected are no longer than 10 inches, the pipe will never contact or damage the translational frame.

A transmission encoding means, such as digital encoder 53 (FIG. 2), is mounted on the base 43 for digitizing the video signals created by the video camera 21. The video signals can be transmitted to the encoder 53 via a coaxial cable (not shown) within the rotating shaft 39, and via a slip joint 55 and slip rings 57. The slip joint 55 and slip rings can be obtained commercially from NDT Systems Incorporated, Odessa, Texas. Digital encoders of the type used in the practice of the invention can be obtained commercially from Klinger Scientific Corporation of Richmond Hill, New York.

Figures 8, 9:
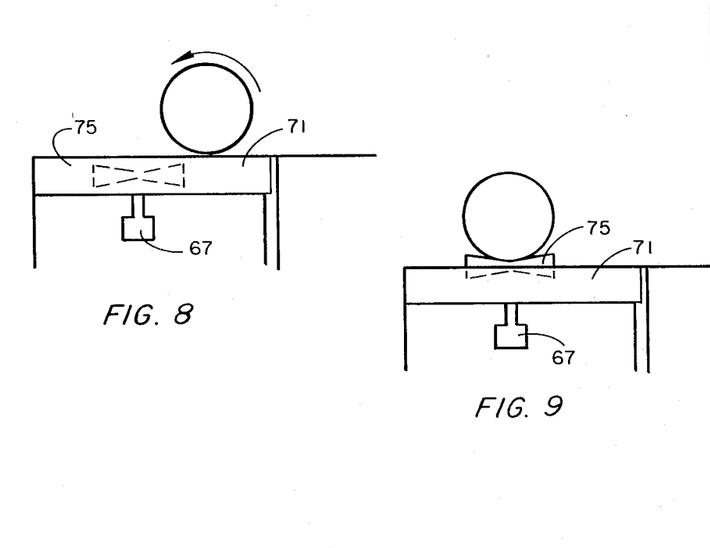
FIG. 8 is an end view of the conveyor schematic of FIG. 5, showing a pipe rolling onto the conveyor.
FIG. 9 is an end view similar to FIG. 6, showing the pipe fully loaded onto the pipe conveyor.
Figure 10:
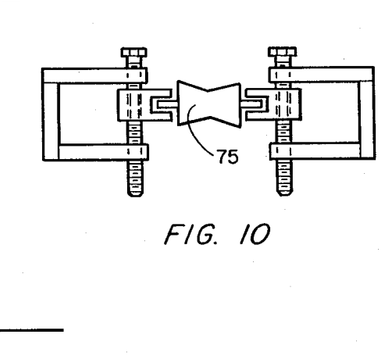
FIG. 10 shows further details of the driven rollers used to move the pipe on the pipe conveyor.

A pipe loading and unloading system can be used to provide and position pipe for the inspection process. This system includes a pipe conveyor 61 (FIG. 7) located adjacent a pipe rack 63. The pipe to be inspected 65 is moved onto the conveyor by hydraulic cylinders 67 which raise and lower bars 71,73. As shown in FIGS. 8 and 9, the bars allow the pipe to be positioned on motor driven rollers 75 so that the pipe can be conveyed linearly in the direction of the pipe receiving opening 51 in the studio and translational frame 31. For pipe of different diameters, it is necessary to either change the height of the rollers 75, or to change the height of the pipe receiving opening 51. (This can be accomplished by raising and lowering the inspection assembly hydraulically.) As shown in FIG. 10, the driven rollers 75 are preferably adjustably mounted on screws 76, 78 between the conveyor sides 80, 82. Turning the screws 76, 78 raises or lowers the rollers 75 to adjust the center line of the pipe being conveyed to the inspection apparatus.

A pipe clamp 77 (FIG. 5) is located intermediate the pipe conveyor 61 and the pipe receiving opening 51 for receiving and securely positioning the pipe 65. The clamp includes jaws 79 which are opened and closed by motor 81. Motor 81 drives a belt 86 which, in turn, drives the jaw positioning screws (88, 90 shown). Photocells 83,85,87 are used to locate the pipe at the correct stopping point so that the threaded surface to be inspected is properly positioned within the pipe receiving opening 51.

The apparatus of the invention also includes a processing means 59 (FIG. 5) which can be located remotely from the remainder of the apparatus. The processing means includes a computer processor for receiving and interpreting the digitized information provided by the transmission encoder 53. The processing means includes a position controller for controlling the movement of the translational frame 31 in response to the digitized information, and an image processor for comparing the digitized information to a programmed standard to determine the thread charcteristics and for detecting defects in the threaded surface being inspected. The processing means 59 is commercially available from the Prothon Division of Video Tek, Inc., of Parsippany, New Jersey.

During the inspection operation, each revolution of the apparatus is encoded via the encoder 53 and the information is provided to the computer 59 which controls the advancement of the translational frame 31 and studio, allowing the video camera 21 to cover the correct number of threads per revolution while assuring 100% linear coverage of the threaded surface. That is, the camera is first positioned at the correct distance from the pipe by the computer position controller. The video camera 21 then begins making pictures of the threads. As the camera 21 spins about the pipe, the computer 59 continues to calculate the distance the camera must be from the threaded surface and commands the translational frame motor 35 to correct if the distance deviates from values obtained from a calibrated test standard which is near perfect round. The computer stores statistical data to compensate for out of roundness of the path of the camera as the translational frame 31 rotates around the pipe threads. The camera can then be calibrated to compensate for out of roundness of the apparatus to accurately measure out of roundness of threads per API tolerance.

As the studio spins about the pipe, light source 11 (FIG. 6) is focused across the threads, cutting across the threads at the tangent of the circle of the threads. Light source 13 shines perpendicular to the axis of the threads but directly onto the threaded surface. As a result, light source 11 can be used to form an optical image of the profile of the threads by the camera, while light source 13 can be used to form a surface optical image of the threads. The profile image can be used to determine the thread lead, thread height, thread taper, pitch diameter, and perfect thread length (API Standard 5B).

Figure 11:
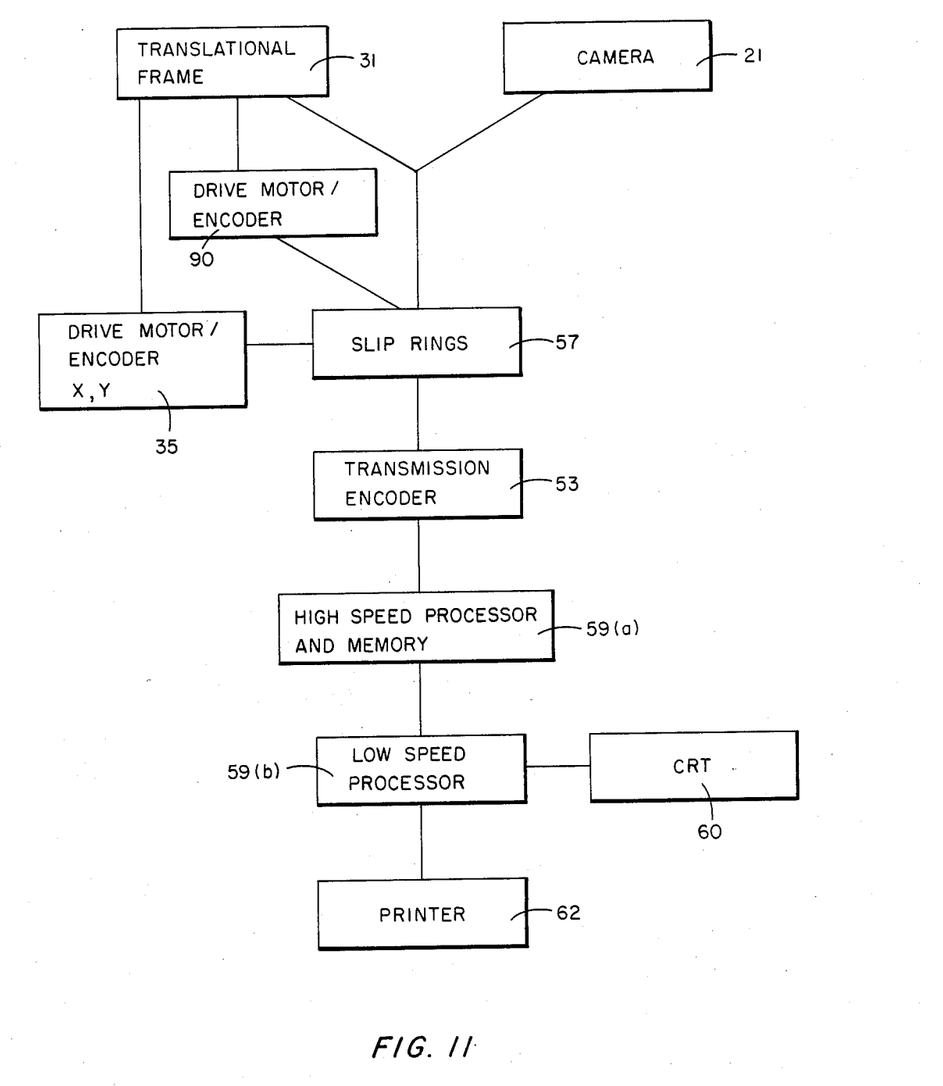
FIG. 11 is a flow diagram which illustrates the operation of the processing means of the apparatus.

These measurements are performed by the video camera 21 taking 60 pictures per second with each picture being analyzed by a high speed processor section (59(a) FIG. 11) of the computer image processor. Each picture is broken down into 350,000 pixels. The intensity of the light directed by the mirrors 15,17,19 to the camera 21 allows values to be assigned to the camera pixels, depending upon which pixels are shaded, partly shaded, or completely illuminated by the light source. As an example, assume full illumination of a pixel results in a reading of 60. If a pixel is blacked out and completely shaded by a portion of the thread form, a reading of 0 results. If ½ of a pixel is illuminated, a reading of 30 is obtained. The image processor 59(a) analyzes the pixel readings and sends this information to a low speed processor 59(b) where the readings are transformed into statistical information. Each frame or picture is compared to the previous and following frames and statistically averaged. The information can be output to a CRT display 60 and/or printer 62. By controlling the revolution rate of the studio, as well as the camera speed, the measurement or inspection density can be controlled.

In the case of the surface optical image, the camera is looking at the thread surface from above the surface. As a result, the scene is wider than the profile view and 100%+ coverage can be maintained. The surface image is used to locate and measure discontinuities and imperfections in the threaded surface. Commonly, these measurements will include skip chatter, saw tooth chatter, shaved threads or flat threads, shoulders, galled threads, torn or mashed threads, cut threads or grinds, tool marks or pits, corroded threads, thread eccentricity or black crest threads and chamfer.

The operation of the apparatus will now be described. The pipe 65 is rolled from the pipe rack 63 onto the conveyor 61 and is conveyed linearly toward the pipe receiving opening 51. As the pipe passes through the jaws 79, photo cell 83 alerts the system to the entrance of the pipe. When photocell 85 is encountered, the system is nearing the stop point and the conveyor speed is slowed. Photocell 87 announces the stop point and simultaneously signals the motor 81 to close the jaws 79 around the pipe.

When the jaws 79 have closed, camera 21 is moved from a retracted position to the start position calculated by the computer 59 for the particular size of pipe being inspected. The computer commands are sent to the drive motor 35 of the translational frame 31 for positioning the camera at the start position. Once the camera is in position, the computer instructs the camera to begin the measuring/inspection process. The camera is then rotated about the circumference of the threaded surface of the pipe by the rotational assembly as the translational frame simultaneously moves the camera linearly along the pipe axis.

An invention has been provided with several advantages. Because the apparatus can scan 360 degrees about the pipe, measurements can be made in multiple planes which encompass all threads. The apparatus also detects minute discontinuities and imperfections in the threads. A 100% inspection of the surface can be provided since contat feelers are not used. The absence of contact feelers also eliminates error introduced by worn feelers or calibration errors. The apparatus of the invention can provide a video picture of the threaded surface being inspected which can be divided into a profile and a head-on surface view of the thread surface. The loca- tion of a defect can be precisely pinpointed and photographed by the video camera. A print-out of the video screen can also be provided. There is no necessity to rotate the pipe being inspected with the present apparatus, and the apparatus can conveniently be installed in a manufacturing plant adjacent a pipe rack.

While the invention has been described in only one of its forms, it should be apparent to those skilled in the art that it is not so limited, but is susceptible to various changes and modifications without departing from the spirit thereof.

I claim:

1. An apparatus for inspecting the externally threaded surface of an object, comprising:
    a studio section including a light source for illuminating the threaded surface to be inspected, a mirror system for directing the light from the light source, and a video camera for receiving the directed light, for forming an optical image of the illuminated threaded surface, and for converting the optical image into electrical video signals;
    positioning means including a translational frame on which the studio section is mounted for moving the studio section in x,y,z planes in order to position the studio section about the object to be inspected at a starting point and for moving the studio section linearly along the longitudinal axis of the object during the inspection process;
    A rotational assembly for spinning the translational frame and studio section circumferentially about the object exterior as the translational frame moves the studio section linearly along the longitudinal axis of the object;
    encoding means for converting the video signals from the video camera into digitized information representative of special information in the optical images viewed by the video camera; and
    processing means for receiving and interpreting the digitized information provided by the encoding means, the processing means including a position controller for controlling the movement of the translational frame in response to the digitized information, and an image processor for comparing the digitized information to a programmed standard for detecting defects in the threaded surface being inspected.

2. The apparatus of claim 1, wherein the object being inspected is a pipe and wherein the studio section includes one light source arranged tangent to the pipe circumference which provides an illuminated profile of the threaded surface being inspected for forming a profile optical image in the video camera and a second light source arranged perpendicular to the pipe central axis which directly illuminates the threaded surface to form a surface optical image in the video camera.

3. The apparatus of claim 1, wherein the rotational assembly includes a rotatable shaft having a yoke at one end for mounting the translational frame, the shaft being mounted on a base having a drive motor for rotating the shaft and, in turn, the translational frame and studio, and wherein the translational frame is provided with a pipe receiving opening axially alignable with a pipe to be inspected when the translational frame is mounted in the rotational assembly.

4. The apparatus of claim 3, further comprising:
    a pipe loading and unloading system including a pipe conveyor which is locatable adjacent a pipe rack, the pipe conveyor having motor driven rollers for moving pipe axially in the direction of the pipe receiving opening in the translational frame.

5. The apparatus of claim 4, further comprising:
    a pipe clamp located intermediate the pipe conveyor and the pipe receiving opening in the translational frame for receiving and securely positioning a pipe to be inspected.

6. The apparatus of claim 3, wherein the rotatable shaft has an end opposite the yoke which carries a slip joint, and wherein the base is provided with a slip ring axially aligned with the slip joint for transmitting the electrical video signals from the rotating studio to the encoding means of the apparatus.

7. A method of inspecting the externally threaded surface of a pipe, comprising the steps of:
    holding a pipe having an end with an externally threaded surface to be inspected stationary while revolving a studio circumferentially about the pipe exterior, the studio being provided with a light source for illuminating the threaded surface to be inspected, a mirror system for directing the light from the light source, and a video camera for receiving the directed light, for forming an optical image of the illuminated threaded surface, and for converting the optical image into electrical video signals; and
    digitizing the electrical video signals with an encoder and providing the digitized signals to a computer processor which interprets and compares the digitized signals to a known standard for determining defects in the threaded surface.

8. The method of claim 7, wherein the computer processor directs a position controller based upon the digitized signals received from the video camera for controlling the movement of the studio in x,y,z planes in order to position the studio about the pipe at a starting point and for moving the studio linearly along the longitudinal axis of the pipe during the inspection process.

9. The method of claim 8, further comprising the steps of:
    directing light from one source tangent to the pipe circumference to provide an illuminated profile of the threaded surface being inspected for forming a profile optical image, and directing light from another source perpendicular to the pipe axis to directly illuminate the threaded surface to provide a surface optical image of the threaded surface being inspected; and
    analyzing both the profile and the surface optical images with the computer processor to provide different types of information about the quality of the threaded surface being inspected.

10. The method of claim 9, further comprising the steps of:
    mounting the studio in a translation frame which can be used to move the studio in x,y,z planes with respect to the external surface of the pipe to be inspected, and mounting the translational frame in a rotational assembly which can be used to rotate the translational frame and studio circumferentially about the pipe exterior as the translational frame moves the studio linearly along the longitudinal axis of the pipe.

11. The method of claim 10, further comprising the steps of:
    providing a pipe receiving opening in the translational frame for receiving an end of a pipe to be inspected; and
    inserting the pipe end into the pipe receiving opening and, while holding the pipe stationary, rotating the translational frame about the pipe.

* * * * *